(12) United States Patent
Kawaguchi et al.

(10) Patent No.: US 8,395,001 B2
(45) Date of Patent: Mar. 12, 2013

(54) PROCESSES FOR PRODUCING 2-CHLORO-1,1,1,2-TETRAFLUOROPROPANE AND 2,3,3,3-TETRAFLUOROPROPENE

(75) Inventors: Satoshi Kawaguchi, Tokyo (JP); Takashi Okazoe, Tokyo (JP); Hidekazu Okamoto, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/157,370

(22) Filed: Jun. 10, 2011

(65) Prior Publication Data

US 2011/0237846 A1    Sep. 29, 2011

Related U.S. Application Data

(63) Continuation of application No. PCT/JP2009/070919, filed on Dec. 15, 2009.

(30) Foreign Application Priority Data

Dec. 16, 2008    (JP) ................................. 2008-319165

(51) Int. Cl.
  *C07C 17/25*    (2006.01)
(52) U.S. Cl. ........ 570/156; 570/165; 570/170; 570/252; 570/260
(58) Field of Classification Search .................. None
See application file for complete search history.

(56) References Cited

U.S. PATENT DOCUMENTS

2007/0197842 A1 *   8/2007   Mukhopadhyay et al. ... 570/155

FOREIGN PATENT DOCUMENTS

| WO | 2007/079431 | 7/2007 |
|---|---|---|
| WO | 2008/040969 | 4/2008 |

OTHER PUBLICATIONS

International Search Report issued Feb. 2, 2010 in PCT/JP09/070919 filed Dec. 15, 2009.
McBee, E. T., et al., "Fluorinated derivatives of propane", Journal of the American Chemical Society, vol. 69, p. 944-947 (1947).
European Search Report in corresponding EPC application 09833439 dated Dec. 17, 2012.
A.L. Henne, et al., "Chlorinated Derivatives of 2-Fluoropropane", Journal of The American Chemical Society, ACS Publications, US, vol. 63, 1941, pp. 2692-2694. XP002427149.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

To provide processes for efficiently and economically producing 2-chloro-1,1,1,2-tetrafluoropropane (R244bb) and 2,3,3,3-tetrafluoropropene (R1234yf) in an industrially practical manner.
A process for producing 2-chloro-1,1,1,2-tetrafluoropropane, which comprises a chlorination step of reacting 1,2-dichloro-2-fluoropropane and chlorine in the presence of a solvent under irradiation with light to obtain 1,1,1,2-tetrachloro-2-fluoropropane, and a fluorination step of reacting the 1,1,1,2-tetrachloro-2-fluoropropane obtained in the chlorination step and hydrogen fluoride in the presence of a catalyst to obtain 2-chloro-1,1,1,2-tetrafluoropropane, and a process for producing 2,3,3,3-tetrafluoropropene, which comprises dehydrochlorinating it in the presence of a catalyst.

20 Claims, No Drawings

PROCESSES FOR PRODUCING 2-CHLORO-1,1,1,2-TETRAFLUOROPROPANE AND 2,3,3,3-TETRAFLUOROPROPENE

TECHNICAL FIELD

The present invention relates to processes for producing 2,3,3,3-tetrafluoropropene which can be utilized as a refrigerant and 2-chloro-1,1,1,2-tetrafluoropropane which is useful as the precursor of such a compound.

BACKGROUND ART

Heretofore, as a refrigerant for air conditioners, a chlorofluorocarbon such as dichlorofluoromethane (R12) or chlorodifluoromethane (R22) has been used, but such a refrigerant has an ozone layer destruction ability or high global warming potential (GWP). Accordingly, in recent years, it has become common to use tetrafluoroethane (R134a) or the like having a low global warming potential as a substitute.

However, recently, reflecting a higher control on greenhouse gas emission, a substitute having a lower GWP is desired, and as the next generation of refrigerant, use of 2,3,3,3-tetrafluoropropene (R1234yf) is being studied.

As a method for producing 2,3,3,3-tetrafluoropropene, a method is known wherein 2-chloro-1,1,1,2-tetrafluoropropane is used as a raw material, and it is dehydrochlorinated. Further, as a method for producing 2-chloro-1,1,1,2-tetrafluoropropane as the raw material, a method of adding hydrogen fluoride to 2-chloro-3,3,3-trifluoropropene ($CH_2=CClCF_3$) (Patent Document 1), or a method of fluorinating chlorine atoms in e.g. fluorotetrachloropropane or dichlorotrifluoropropane (Patent Document 2) is, for example, known.

In the method disclosed in Patent Document 1, going further back to obtain 2-chloro-3,3,3-trifluoropropene, four-step reactions are carried out by using 2,3-dichloropropene as the starting material, and if this 2,3-dichloropropene is taken as the starting material, in order to obtain 2,3,3,3-tetrafluoropropene as the desired material, six-step reactions are required. Thus, the method disclosed in Patent Document 1 had a problem that the number of steps are many, and the production cost tends to be accordingly high. Further, in this method, a step of dehydrochlorination employing an alkali, is essential, and there is also a problem such that a large amount of waste water is generated. Further, also the method disclosed in Patent Document 2 had a problem that it can hardly be carried out on an industrial scale, since many steps are required for the synthesis of the raw material, and a highly toxic chemical substance is used.

As described above, with respect to 2,3,3,3-tetrafluoropropene (R1234yf) which is expected as the next generation of refrigerant, various production methods have been proposed, but a method for producing it efficiently on an industry scale has not yet been known.

PRIOR ART DOCUMENTS

Patent Documents

Patent Document 1: WO2007/079431
Patent Document 2: WO2008/040969

DISCLOSURE OF INVENTION

Technical Problem

The present invention has been made from the above-described viewpoint, and it is an object of the present invention to provide processes for efficiently and economically producing 2-chloro-1,1,1,2-tetrafluoropropane (R244bb) and 2,3,3,3-tetrafluoropropene (R1234yf) in an industrially practical manner.

Solution to Problem

The present invention provides a process for producing 2-chloro-1,1,1,2-tetrafluoropropane, characterized by comprising a chlorination step of reacting 1,2-dichloro-2-fluoropropane and chlorine in the presence of a solvent under irradiation with light to obtain 1,1,1,2-tetrachloro-2-fluoropropane, and a fluorination step of reacting the 1,1,1,2-tetrachloro-2-fluoropropane obtained in the chlorination step and hydrogen fluoride in the presence of a catalyst to obtain 2-chloro-1,1,1,2-tetrafluoropropane.

Further, the present invention provides a process for producing 2,3,3,3-tetrafluoropropene, which comprises subjecting the 2-chloro-1,1,1,2-tetrafluoropropane obtained by the above process of the present invention to a dehydrochlorination reaction in the presence of a catalyst.

ADVANTAGEOUS EFFECTS OF INVENTION

According to the processes of the present invention, it is possible to efficiently and economically produce 2-chloro-1,1,1,2-tetrafluoropropane (R244bb) and 2,3,3,3-tetrafluoropropene (R1234yf) in an industrially practical manner.

DESCRIPTION OF EMBODIMENTS

Now, embodiments of the present invention will be described.

Firstly, with respect to the process for producing 2-chloro-1,1,1,2-tetrafluoropropane (R244bb) of the present invention, an embodiment will be described. In this specification, with respect to a halogenated hydrocarbon, the compound name will be followed by an abbreviated name of the compound in brackets, but in this specification, instead of the compound name, its abbreviated name may be employed as the case requires.

<Process for Producing 2-chloro-1,1,1,2-tetrafluoropropane (R244bb)>

The process for producing 2-chloro-1,1,1,2-tetrafluoropropane (R244bb) of the present invention comprises the following chlorination step and fluorination step.

(1) Chlorination Step

In the chlorination step in the process for producing R244bb of the present invention, as shown by the following reaction formula (1), 1,2-dichloro-2-fluoropropane (R261ba, $CH_3CClFCH_2Cl$) and chlorine are reacted in the presence of a solvent under irradiation with light to form 1,1,1,2-tetrachloro-2-fluoropropane (R241bb, $CH_3CClFCCl_3$).

[Reaction Formula of Chlorination Step]

$$CH_3CClFCH_2Cl + 2Cl_2 \rightarrow CH_3CClFCCl_3 + 2HCl \qquad (1)$$

1,2-dichloro-2-fluoropropane (R261ba, $CH_3CClFCH_2Cl$) to be used as a starting material in the reaction in the chlorination step shown by the above reaction formula (1) can be produced by a known method. Specifically, using, as the raw material, 2,3-dichloropropene ($CH_2=CClCH_2Cl$) available also as a commercial product, it can be produced by reacting this compound with hydrogen fluoride under usual conditions.

In the reaction in the chlorination step shown by the above reaction formula (1), 1,2-dichloro-2-fluoropropane (R261ba, $CH_3CClFCH_2Cl$) thus obtained, and chlorine are reacted, and this reaction is carried out in the presence of a solvent under irradiation with light.

In the reaction in the chlorination step in the process for producing R244bb of the present invention, by the presence of a solvent, solid R241bb formed can be dissolved, whereby the reaction can be carried out in a homogeneous system. As the solvent to be used for the reaction in the chlorination step, a solvent which is capable of dissolving the raw material components (1,2-dichloro-2-fluoropropane (R261ba) and chlorine) and inert to the raw material components and which can easily be separated from the desired product (1,1,1,2-tetrachloro-2-fluoropropane (R241bb)) by e.g. distillation, may be mentioned without any particular restriction.

Further, as such a solvent, specifically, carbon tetrachloride, 1,1,2-trichloro-1,2,2-trifluoroethane (R113), a $C_{5-8}$ linear perfluoroalkyl compound represented by $CF_3(CF_2)_nCF_3$ (wherein n is an integer of from 3 to 6), or a perhalogenated compound such as hexachloroacetone may be mentioned. Among these solvents, in the present invention, carbon tetrachloride (boiling point: 76.8° C.) is preferably employed, since it is inexpensive and has a sufficient difference in boiling point from the desired product 1,1,1,2-tetrachloro-2-fluoropropane (R241bb, boiling point: 140° C.).

The amount of the solvent to be used for the reaction in the chlorination step shown by the above reaction formula (1) is not particularly limited so long as R241bb formed can thereby be dissolved, but specifically, it is from 1 to 1,000 mass %, preferably from 50 to 100 mass %, based on the raw material components (the total amount of 1,2-dichloro-2-fluoropropane (R261ba) and chlorine).

In the reaction in the chlorination step shown by the above reaction formula (1), the irradiation with light is essential to induce the reaction. Specifically, the light for the irradiation may, for example, be ultraviolet light containing light with a wavelength of from 200 to 400 nm. In the reaction shown by the above reaction formula (1), a light source capable of carrying out such irradiation with light may, for example, be a high pressure mercury lamp, a low pressure mercury lamp or a metal halide lamp.

The method for irradiation with light is not particularly limited so long as it is a method whereby the entire reaction liquid can be uniformly irradiated throughout the reaction time. However, for example, a method may be mentioned wherein a light source provided with a jacket made of a corrosion-resistant material which permeates at least light with wavelength required for the above reaction and is inert to the reaction liquid components, is inserted in the reaction liquid to apply light to the reaction liquid from inside of the reaction liquid. Further, in a case where the light source generates a heat, the above jacket may preferably be a jacket having a cooling means, depending upon the reaction temperature.

The reaction temperature in the reaction in the chlorination step shown by the above reaction formula (1) is suitably adjusted by the pressure conditions during the reaction. With respect to the reaction condition for the reaction shown by the above reaction formula (1), for example, in a case where pressurization is required for the purpose of e.g. shortening of the reaction time or suppressing the evaporation of the content, it may be a pressure condition of at most 1.0 MPa, or the internal pressure in the reactor may be from ordinary pressure to 1.0 MPa. However, from the viewpoint of industrial operation efficiency, it is preferred to carry out the reaction under ordinary pressure without controlling the pressure. The reaction temperature in the case of carrying out the reaction shown by the above reaction formula (1) under ordinary pressure, is preferably from −20 to 60° C., more preferably from 0 to 10° C., from the viewpoint of the reaction rate and the selectivity.

The reaction in the chlorination step shown by the above reaction formula (1) may be carried out by a method of either batch system or continuous flow system. The reaction time may suitably be adjusted by a usual method depending upon each system. Feeding of chlorine to the reaction system i.e. to the mixture containing the prescribed amounts of 1,2-dichloro-2-fluoropropane (R261ba) and the solvent, can be carried out by a method of diluting chlorine with an inert gas such as nitrogen as the case requires and blowing a prescribed amount per hour during the reaction, to the reaction liquid intermittently or continuously, or by a method of charging it to a mixture of prescribed amounts of 1,2-dichloro-2-fluoropropane (R261ba) and the solvent in a pressurized state prior to the reaction. Further, at the time of the reaction in the chlorination step shown by the above reaction formula (1), it is preferred to add a stirring operation by means of a usual method, apparatus, etc.

The material for the reactor to carry out the reaction in the chlorination step shown by the above reaction formula (1) may, for example, be a material which is usually used in e.g. a chemical reaction similar to the reaction shown by the reaction formula (1), e.g. glass, iron, nickel or an alloy containing such metal as the main component.

Further, in the reaction in the chlorination step shown by the above reaction formula (1), even if the above-mentioned various reaction conditions are adjusted, in the reaction liquid at the stage where all the raw material component 1,2-dichloro-2-fluoropropane (R261ba) has been reacted and the conversion has become 100%, there exist, in addition to the desired product 1,1,1,2-tetrachloro-2-fluoropropane (R241bb, $CH_3CClFCCl_3$, the yield at the time when the reaction is carried out under preferred conditions, such as at 5° C. under ultraviolet irradiation by a high pressure mercury lamp (500 W): about 65.3%), ones formed as side reaction products (such as a low chlorinated product 1,1,2-trichloro-2-fluoropropane ($CH_3CClFCHCl_2$, yield under the above reaction conditions: about 7.2%) or 1,2,3-trichloro-2-fluoropropane ($CH_2ClCClFCH_2Cl$, yield under the above reaction conditions: about 1.4%), and, as an isomer of the desired product, 1,1,2,3-tetrachloro-2-fluoropropane ($CH_2ClCClFCHCl_2$, yield under the above reaction conditions: about 12.0%), etc. Here, "yield" used in this specification is meant for the yield calculated from the peak area obtained as a result of the gas chromatography measurement.

Among these side reaction products, there may be side reaction products which can be separated from the desired product (R241bb) by a usual method such as distillation, but 1,1,2,3-tetrachloro-2-fluoropropane as an isomer of the desired product (R241bb) has a small difference in boiling point from the desired product (R241bb), and its production amount is substantial, and it is a side reaction product which is most difficult to separate. In the reaction in the chlorination step in the process of the present invention, it is preferred to lower the content, in the reaction liquid, of 1,1,2,3-tetrachloro-2-fluoropropane as one of the above-mentioned side reaction products with a view to separating and purifying the desired product (R241bb) to a high purity by a simple process. As a specific method, a method may be mentioned wherein introduction of chlorine into the reaction system is continuously carried out or additionally carried out even after 100% conversion of 1,2-dichloro-2-fluoropropane (R261ba) as the raw material component, thereby to chlorinate and convert 1,1,2,3-tetrachloro-2-fluoropropane ($CH_2ClCClFCHCl_2$) as an isomer of the desired product (R241bb)

present in the reaction liquid to e.g. 1,1,1,2,3-pentachloro-2-fluoropropane ($CH_2ClCClFCHCl_3$) and thereby to let chlorination proceed until the content of 1,1,2,3-tetrachloro-2-fluoropropane becomes to a yield of less than 1% in the reaction product.

Here, when introduction of chlorine into the above reaction system is carried out continuously even after 100% conversion of 1,2-dichloro-2-fluoropropane (R261ba) as the raw material component, a chlorination reaction of 1,1,1,2-tetrachloro-2-fluoropropane (R241bb) as the desired product may occur in parallel, whereby 1,1,1,2,3-pentachloro-2-fluoropropane ($CH_2ClCClFCCl_3$), 1,1,1,2,3,3-hexachloro-2-fluoropropane ($CHCl_2CClFCCl_3$), etc. will be formed anew as side reaction products. However, the chlorination reaction of 1,1,2,3-tetrachloro-2-fluoropropane as an isomer of the desired product (R241bb) proceeds more selectively and specifically than the chlorination reaction of the desired product (R241bb), and accordingly, even if the chlorination reaction is carried out until 1,1,2,3-tetrachloro-2-fluoropropane as an isomer of the desired product becomes an yield of less than 1% in the reaction product, the decrease in the yield of the desired product (R241bb) is as small as a non-problematic level.

Further, it is possible to confirm the change with time of the yield (content) of each compound in the reaction system by installing an analytical equipment such as gas chromatography on the reaction apparatus and carrying out the continuous measurement, and it becomes possible to thereby control the reaction.

In the chlorination step in the process for producing R244bb of the present invention, then, 1,1,1,2-tetrachloro-2-fluoropropane (R241bb) is separated and purified by a usual method such as distillation from the reaction liquid having the content of 1,1,2,3-tetrachloro-2-fluoropropane as an isomer of 1,1,1,2-tetrachloro-2-fluoropropane (R241bb) thus obtained, reduced preferably to a yield of less than 1%.

(2) Fluorination Step

In the fluorination step in the process for producing R244bb of the present invention, as shown by the following reaction formula (2), 1,1,1,2-tetrachloro-2-fluoropropane (R241bb, $CH_3CClFCCl_3$) obtained in the above chlorination step and hydrogen fluoride are reacted in the presence of a catalyst to form 2-chloro-1,1,1,2-tetrafluoropropane (R244bb, $CH_3CClFCF_3$).

[Reaction Formula of Fluorination Step]

$$CH_3CClFCCl_3 + 3HF \rightarrow CH_3CClFCF_3 + 3HCl \quad (2)$$

As the catalyst to be used for the reaction in the fluorination step shown by the above reaction formula (2) in the process for producing R244bb of the present invention, a catalyst which is commonly used for fluorination of a hydrocarbon compound may be mentioned without any particular restriction. As such a catalyst, specifically, a catalyst for fluorination which contains at least one metal halide selected from e.g. antimony, niobium, tantalum, tin, titanium, iron and thallium is preferred, and more preferably, a catalyst for fluorination which contains antimony pentachloride ($SbCl_5$) may be mentioned.

Further, the amount of the catalyst to be used for the reaction in the fluorination step shown by the above reaction formula (2), is, as the amount of the above-mentioned metal halide, preferably an amount of from 0.1 to 100 mol %, more preferably an amount of from 0.1 to 10 mol %, based on the reaction raw material component (1,1,1,2-tetrachloro-2-fluoropropane (R241bb)).

The reaction temperature in the reaction in the fluorination step shown by the above reaction formula (2) is suitably adjusted by the pressure conditions during the reaction. With respect to the pressure conditions for the reaction shown by the above reaction formula (2), for example, in a case where pressurization is required for the purpose of shortening of the reaction time or letting the hydrogen fluoride as the reaction raw material component be present in the liquid phase, it is possible to adjust the pressure condition to be at most 10 MPa or to adjust the internal pressure in the reactor to be from ordinary pressure to 10 MPa. However, a pressure condition of at most 4.0 MPa, or the internal pressure in the reactor being from ordinary pressure to 4.0 MPa is preferred from the viewpoint of industrial practical efficiency. The reaction shown by the above reaction formula (2) is preferably carried out at a temperature of from 50 to 200° C. from the viewpoint of the reaction rate and the selectivity, and from 80 to 120° C. is a more preferred reaction temperature.

The reaction in the fluorination step shown by the above reaction formula (2) may be carried out by a method of either batch system or continuous flow system. Further, the reaction time may suitably be adjusted by a usual method depending upon each system. Feeding of hydrogen fluoride to the reaction system i.e. to the mixture containing the respective prescribed amounts of 1,1,1,2-tetrachloro-2-fluoropropane (R241bb) and the catalyst is carried out, in a batch system, usually by a method of cooling the above mixture by e.g. liquid nitrogen under reduced pressure to such an extent that hydrogen fluoride will not vaporize and introducing a prescribed amount of hydrogen fluoride under reduced pressure, taking into the boiling point (19.5° C.) of hydrogen fluoride into consideration. Further, it is preferred that hydrogen chloride (gas) formed as a byproduct during the reaction in the fluorination step shown by the above reaction formula (2) is taken out of the reaction system and recovered by a suitable method. Further, at the time of the reaction in the fluorination step shown by the above reaction formula (2), it is preferred to add a stirring operation by means of a usual method, apparatus, etc.

The material for the reactor to carry out the reaction in the fluorination step shown by the above reaction formula (2) may, for example, be a material which is usually used in e.g. a chemical reaction similar to the reaction shown by the reaction formula (2), e.g. glass, iron, nickel or an alloy containing such metal as the main component.

Further, in the reaction in the fluorination step shown by the above reaction formula (2), the desired product 2-chloro-1,1,1,2-tetrafluoropropane (R244bb, $CH_3CClFCF_3$) is obtained in the gaseous state at ordinary temperature and pressure under the above exemplified reaction conditions, but even when the reaction conditions are adjusted to be preferable ones, in the reaction product gas at the stage where all the raw material component 1,1,1,2-tetrachloro-2-fluoropropane (R241bb) has been reacted, and the conversion has become 100%, there exist, in addition to the desired product 2-chloro-1,1,1,2-tetrafluoropropane (R244bb, $CH_3CClFCF_3$, the yield at the time when the reaction is carried out under preferred conditions, such as under 0.95 MPa at from 80 to 90° C.: about 47%), ones formed as side reaction products, such as 1,2-dichloro-1,1,2-trifluoropropane ($CH_3CClFClF_2$, yield under the above reaction conditions: about 11%), 3,3,3-trifluoro-2-chloropropene ($CH_2=CClCF_3$, yield under the above reaction conditions: about 11%), 2,2-dichloro-1,1,1-trifluoropropane ($CH_3CCl_2CF_3$, yield under the above reaction conditions: about 20%), etc.

Each of these side reaction products is a side reaction product which can be separated from the desired product (R244bb) by a usual method such as distillation, whereby the desired product 2-chloro-1,1,1,2-tetrafluoropropane (R244bb) can be separated and purified from the reaction product gas by a usual method such as distillation, and used.

Further, each of the above side reaction products 1,2-dichloro-1,1,2-trifluoropropane, 3,3,3-trifluoro-2-chloropropene and 2,2-dichloro-1,1,1-trifluoropropane, can be converted to 2-chloro-1,1,1,2-tetrafluoropropane (R244bb) as the desired product in the process of the present invention, as shown by the following reaction formula (3), (4) or (5), by separating it from the desired product (R244bb) and then carrying out a fluorination reaction using it as the starting material under the conditions of a fluorination reaction similar to those described above.

[Reaction Formulae for Fluorination of Side Reaction Products]

$$CH_3CClFClF_2 + HF \rightarrow CH_3CClFCF_3 + HCl \quad (3)$$

$$CH_2=CClCF_3 + HF \rightarrow CH_3CClFCF_3 \quad (4)$$

$$CH_3CCl_2CF_3 + HF \rightarrow CH_3CClFCF_3 + HCl \quad (5)$$

Thus, for example, when the reaction in the fluorination step shown by the above reaction formula (2) is carried out by a continuous flow system, a crude gas recovered as the reaction product from the reactor is separated into the desired product (R244bb) and the side reaction product, and the obtained side reaction product is subjected to recycle use (reaction) by feeding it to the reactor as mixed to R241bb as the reaction raw material component, whereby it is possible to obtain R244bb from the side reaction product together with the reaction product R244bb from R241bb. Otherwise, recycle use (reaction) may be carried out in such a manner as to obtain R244bb by reacting only the above side reaction product alone with hydrogen fluoride in the presence of a catalyst in a reactor separate from R241bb.

The fluorination step to obtain 2-chloro-1,1,1,2-tetrafluoropropane (R244bb) by reacting 1,1,1,2-tetrachloro-2-fluoropropane (R241bb) with hydrogen fluoride in the presence of a catalyst in the process for producing R244bb of the present invention, includes a fluorination reaction wherein side reaction products obtainable by reacting such 1,1,1,2-tetrachloro-2-fluoropropane (R241bb) with hydrogen fluoride, such as 1,2-dichloro-1,1,2-trifluoropropane, 3,3,3-trifluoro-2-chloropropene and 2,2-dichloro-1,1,1-trifluoropropane, are further recycled and reacted with hydrogen fluoride in the presence of a catalyst to form 2-chloro-1,1,1,2-tetrafluoropropane (R244bb).

Next, with respect to the process for producing 2,3,3,3-tetrafluoropropene (R1234yf) of the present invention by using 2-chloro-1,1,1,2-tetrafluoropropane (R244bb) obtained by the above-described process of the present invention, an embodiment will be described.

<Process for Producing 2,3,3,3-tetrafluoropropene (R1234yf)>

The process for producing 2,3,3,3-tetrafluoropropene (R1234yf, $CH_2=CFCF_3$) of the present invention is characterized by subjecting 2-chloro-1,1,1,2-tetrafluoropropane (R244bb, $CH_3CClFCF_3$) obtainable by the above-described process of the present invention to a dehydrochlorination reaction as shown by the following reaction formula (6) in the presence of a catalyst to obtain 2,3,3,3-tetrafluoropropene.

[Reaction Formula For Dehydrochlorination Of R244bb]

$$CH_3CClFCF_3 \rightarrow CH_2=CFCF_3 + HCl \quad (6)$$

In the process for producing R1234yf of the present invention, the dehydrochlorination reaction of the above reaction formula (6) can be carried out by a conventional method by means of a conventional catalyst. As such a catalyst, specifically, activated carbon, a nickel catalyst (such as nickel mesh) or a combination thereof may, for example, be mentioned. As other catalysts, palladium-supported carbon, palladium-supported alumina, etc. may be used. Such a catalyst is employed as packed in the form of a fixed bed or a fluidized bed in the reactor.

The reaction temperature in the dehydrochlorination reaction shown by the above reaction formula (6) is suitably adjusted by the pressure condition during the reaction. With respect to the pressure condition for the reaction shown by the above reaction formula (6), for example, in a case where pressurizing is required for the purpose of e.g. shortening of the reaction time, a pressure condition of at most 1.0 MPa; or an internal pressure in the reactor of from ordinary pressure to 1.0 MPa may be adopted, but from the viewpoint of industrial operation efficiency, it is preferred to carry out the reaction under ordinary pressure without carrying out the pressure adjustment. In the case of carrying out the dehydrochlorination reaction shown by the above reaction formula (6) under ordinary pressure, the reaction temperature is preferably adjusted to be from 200 to 700° C., more preferably from 350 to 450° C.

The dehydrochlorination reaction shown by the above reaction formula (6) may be carried out by either a batch system or a continuous flow system, but from the viewpoint of the production efficiency, a continuous flow system is preferred. Further, the reaction time can be suitably adjusted by a usual method depending upon each system. Further, at the time of the dehydrochlorination reaction shown by the above reaction formula (6), it is preferred to add a stirring operation by means of a usual method, apparatus, etc.

The dehydrochlorination reaction shown by the above reaction formula (6) is carried out usually in a gas phase. As the material for a gas phase reactor to be used for such a reaction, a usual material such as stainless steel, Hastelloy (registered trademark) being a nickel alloy, Inconel (registered trademark), Monel (registered trademark), a metal lined with a fluorinated polymer, or glass may be mentioned.

EXAMPLES

Now, the present invention will be described in detail with reference to Examples, but it should be understood that the present invention is by no means thereby restricted. In the following description of Examples, gas chromatography is represented by GC, the purity calculated from the peak area ratio of GC is represented by GC purity, and the yield calculated from the peak area ratio of GC is represented by GC yield.

Further, the selectivity (%) is meant for the mass % of a specific reaction product in the total amount of the mixture of reaction products obtained from the reaction raw material.

Example 1

Production of 2-chloro-1,1,1,2-tetrafluoropropane ($CH_3CClFCF_3$ (R244bb))

(1) Synthesis of 1,2-dichloro-2-fluoropropane ($CH_3CClFCH_2Cl$ (R261ba)) as Raw Material Component in Chlorination Step Into an autoclave and having an internal capacity of 2 L, 1017 g of 2,3-dichloropropene ($CH_2=CClCH_2Cl$) was charged. This autoclave was cooled by liquid nitrogen, and then, 459 g of hydrogen fluoride was introduced to 2,3-dichloropropene in the autoclave under reduced pressure.

Then, stirring was carried out for 13 hours while the internal temperature of the autoclave was maintained to be from 50° C. to 60° C. After completion of the stirring, the autoclave was cooled so that the internal temperature became 5° C., whereupon the obtained reaction crude product was poured into ice water. The organic layer of the reaction crude product was washed with water in the ice water, and anhydrous magnesium sulfate was added thereto for drying, followed by filtration to obtain 986 g of a reaction crude liquid.

As a result of a GC analysis of the reaction crude liquid thus obtained, the reaction crude liquid was found to contain, as GC yield, 86.5% of 1,2-dichloro-2-fluoropropane ($CH_3CClFCH_2Cl$ (R261ba)), 3.9% of 1,2,2-trichloropropane ($CH_3CCl_2CH_2Cl$) and 5.1% of 1-chloro-2,2-difluoropropane ($CH_3CF_2CH_2Cl$). The reaction crude liquid was distilled under reduced pressure to recover 1,2-dichloro-2-fluoropropane ($CH_3CClFCH_2Cl$ (R261ba)) as a fraction. The GC purity of R261ba in the fraction was 99.4%.

(2) Chlorination Step (Synthesis of 1,1,1,2-tetrachloro-2-fluoropropane ($CH_3CClFCCl_3$ (R241bb))

Into a high pressure mercury lamp-provided glass reactor having an internal capacity of 100 mL and equipped with a condenser (the high pressure mercury lamp (output power: 500 W, ultraviolet emission light source to emit light with a wavelength of from 200 to 400 nm) as the light source had a quartz jacket), a stirrer was put, and 40.5 g of the 1,2-dichloro-2-fluoropropane ($CH_3CClFCH_2Cl$ (R261ba)) fraction (GC purity of R261ba: 99.4%) obtained in the above (1) and 40.1 g of carbon tetrachloride was charged. While chlorine gas was introduced at a rate of 6 g/hr into the liquid in this reactor, and cooling was carried out so that the internal temperature could not exceed 5° C., light irradiation was carried out for 4.5 hours. Here, during the light irradiation, the light source was cooled by circulating cooling water in the jacket made of quartz. After completion of the reaction, the reaction crude product (93.3 g) was recovered and subjected to washing with water to remove dissolved chlorine gas thereby to obtain a reaction crude liquid.

Further, in the above reaction, upon expiration of 3.5 hours from the initiation of the light irradiation reaction, the conversion of 1,2-dichloro-2-fluoropropane (R261ba, $CH_3CClFCH_2Cl$) as the raw material component was 100%, and the GC yield of the desired product (R241bb) was 65.3%, but at that time, the GC yield of 1,1,2,3-tetrachloro-2-fluoropropane ($CH_2ClCClFCHCl_2$) being an isomer of R241bb which is a side reaction product and is difficult to separate from the desired product, was as high as 12.0%. Therefore, the chlorination reaction by light irradiation was carried out continuously, and finally, the chlorination reaction by light irradiation was terminated upon expiration of 4.5 hours. Further, in the reaction crude liquid upon expiration of 3.5 hours from the initiation of the reaction, as other components, 7.2% by GC yield of 1,1,2-trichloro-2-fluoropropane ($CH_3CClFCHCl_2$), and 1.4% by GC yield of 1,2,3-trichloro-2-fluoropropane ($CH_2ClCClFCH_2Cl$) were contained.

As a result of a GC analysis of the reaction crude liquid thus obtained, the conversion of 1,2-dichloro-2-fluoropropane ($CH_3CClFCH_2Cl$) was 100%. Further, the GC yield of 1,1,1, 2-tetrachloro-2-fluoropropane ($CH_3CClFCCl_3$ (R241bb)) in the reaction crude liquid was 65.3%. Further, in the reaction crude liquid, as other components, 0.2% by GC yield of 1,1,2,3-tetrachloro-2-fluoropropane ($CH_2ClCClFCHCl_2$) which was 12.0% by GC yield upon expiration of the reaction time of 3.5 hours, 8.4% by GC yield of 1,1,2,3,3-pentachloro-2-fluoropropane ($CHCl_2CClFCHCl_2$), 19.3% by GC yield of 1,1,1,2,3-pentachloro-2-fluoropropane ($CH_2ClCClFCCl_3$) and 8.7% by GC yield of 1,1,1,2,3,3-hexachloro-2-fluoropropane ($CHCl_2CClFCCl_3$) were contained. Further, 1,1,2-trichloro-2-fluoropropane ($CH_3CClFCHCl_2$) and 1,2,3-trichloro-2-fluoropropane ($CH_2ClCClFCH_2Cl$) which were present in the reaction crude liquid upon expiration of the reaction time of 3.5 hours, were not contained in the reaction crude liquid recovered finally after completion of the reaction. The reaction crude liquid was distilled under reduced pressure to recover 1,1,1,2-tetrachloro-2-fluoropropane ($CH_3CClFCCl_3$ (R241bb)) as a fraction. The GC purity of R241bb in the fraction was 96%.

(3) Fluorination Step (Synthesis of 2-chloro-1,1,1,2-tetrafluoropropane ($CH_3CClFCF_3$ (R244bb))

Into an autoclave made of Hastelloy, having an internal capacity of 200 mL and equipped with a condenser, 18.6 g of the 1,1,1,2-tetrachloro-2-fluoropropane ($CH_3CClFCCl_3$ (R241bb)) fraction (GC purity of R241bb: 96%) obtained in the above (2) and 3.47 g of antimony pentachloride were charged and cooled in a liquid nitrogen bath. Then, 71.7 g of hydrogen fluoride was introduced into the autoclave under reduced pressure, and then, while the internal temperature was maintained to be from 80° C. to 90° C., hydrogen chloride formed as a byproduct was timely released, and stirring was continued for 5 hours while the internal pressure was maintained to be 0.95 MPa. After completion of the reaction, the internal temperature of the autoclave was returned to room temperature, and then, the valve at the outlet of the condenser was opened to take out the reaction product crude gas, which was passed through a 10% potassium hydroxide aqueous solution and then collected as a reaction crude gas in a cylinder.

As a result of a GC analysis of the reaction crude gas thus obtained, the conversion of 1,1,1,2-tetrachloro-2-fluoropropane ($CH_3CClFCCl_3$ (R241bb)) was 100%. Further, the GC yield of 2-chloro-1,1,1,2-tetrafluoropropane ($CH_3CClFCF_3$ (R244bb)) in the reaction crude gas was 47.4%, and the selectivity was 48.3%. Further, in the reaction crude gas, in addition to the desired product (R244bb), as side reaction products convertible to the desired product (R244bb), 11% by GC yield of 1,2-dichloro-1,1,2-trifluoropropane ($CH_3CClFClF_2$), 11% by GC yield of 3,3,3-trifluoro-2-chloropropene ($CH_2=CClCF_3$) and 20% by GC yield of 2,2-dichloro-1,1,1-trifluoropropane ($CH_3CCl_2CF_3$) were contained, and if such side reaction products are included, the selectivity for the reaction for 2-chloro-1,1,1,2-tetrafluoropropane (R244bb) may be said to be 79.8%.

Example 2

Production of 2,3,3,3-tetrafluoropropene ($CH=CFCF_3$ (R1234yf))

Into a gas phase reactor made of Inconel (registered trademark) and having a radius of ¼ inch, activated carbon (2.12 g) was packed as a catalyst. A preheater was attached to the reactor, and the temperature was maintained to be 400° C. To this gas phase reactor, 10 g of the reaction crude gas containing 2-chloro-1,1,1,2-tetrafluoropropane ($CH_3CClFCF_3$ (R244bb)) obtained in the above Example 1 was supplied from a cylinder maintained at a temperature of 65° C. via a mass flow controller and a preheater. The temperature in the line from the cylinder via the mass flow controller to the preheater was maintained to be 65° C. to prevent condensation of 2-chloro-1,1,1,2-tetrafluoropropane (CH$_3$CClFCF$_3$ (R244bb)).

The 2-chloro-1,1,1,2-tetrafluoropropane (R244bb) supplied to the above gas phase reactor was contacted with an activated carbon catalyst while passing through the gas phase reactor (passing through time: 1 second) under a condition of a reaction temperature of 400° C. and dehydrochlorinated to form 2,3,3,3-tetrafluoropropene (CH=CFCF$_3$ (R1234yf)), and the reaction product crude gas containing such R1234yf was recovered from the outlet of the above gas phase reactor. With respect to the reaction product crude gas recovered, a GC analysis was carried out, whereby the conversion of 2-chloro-1,1,1,2-tetrafluoropropane (CH$_3$CClFCF$_3$ (R244bb)) was 85%. Further, the GC yield of 2,3,3,3-tetrafluoropropene (CH=CFCF$_3$ (R1234yf)) in the reaction product crude gas was 63%, and the selectivity was 74%.

INDUSTRIAL APPLICABILITY 2-chloro-1,1,1,2-tetrafluoropropane (R244bb) which is efficiently and economically produced in an industrially practical manner by the present invention, is useful as a precursor for 2,3,3,3-tetrafluoropropene (R1234yf), and 2,3,3,3-tetrafluoropropene (R1234yf) can be effectively utilized as a refrigerant for e.g. a room air conditioner or a car air conditioner, or as a fluorinated monomer.

The entire disclosure of Japanese Patent Application No. 2008-319165 filed on Dec. 16, 2008 including specification, claims, drawings and summary is incorporated herein by reference in its entirety.

What is claimed is:

1. A process for producing 2-chloro-1,1,1,2-tetrafluoropropane, comprising:
a chlorination step of reacting 1,2-dichloro-2-fluoropropane and chlorine in the presence of a solvent under irradiation with light to obtain 1,1,1,2-tetrachloro-2-fluoropropane, and
a fluorination step of reacting the 1,1,1,2-tetrachloro-2-fluoropropane obtained in the chlorination step and hydrogen fluoride in the presence of a catalyst to obtain 2-chloro-1,1,1,2-tetrafluoropropane,
wherein the solvent comprises at least one member selected from the group consisting of carbon tetrachloride, 1,1,2-trichloro-1,2,2-trifluoroethane, a C$_{5-8}$ linear perfluoroalkyl compound represented by the formula CF$_3$(CF$_2$)$_n$CF$_3$, wherein n is an integer of from 3 to 6, and a perhalogenated compound, and
wherein the catalyst comprises at least one halide of a metal selected from the group consisting of antimony, niobium, tantalum, tin, titanium, iron and thallium.

2. The process for producing 2-chloro-1,1,1,2-tetrafluoropropane according to claim 1, wherein the solvent in the chlorination step is carbon tetrachloride.

3. The process for producing 2-chloro-1,1,1,2-tetrafluoropropane according to claim 1, wherein the light for the irradiation with light in the chlorination step is ultraviolet light containing light with a wavelength of from 200 to 400 nm.

4. The process for producing 2-chloro-1,1,1,2-tetrafluoropropane according to claim 1, wherein the reaction temperature in the chlorination step is from −20 to 60° C.

5. The process for producing 2-chloro-1,1,1,2-tetrafluoropropane according to claim 1, wherein the catalyst in the fluorination step is a catalyst for fluorination is at least one halide of a metal selected from antimony, niobium, tantalum, tin, titanium, iron and thallium.

6. The process for producing 2-chloro-1,1,1,2-tetrafluoropropane according to claim 1, wherein the reaction temperature in the fluorination step is from 50 to 200° C.

7. A process for producing 2,3,3,3-tetrafluoropropene, which comprises subjecting the 2-chloro-1,1,1,2-tetrafluoropropane obtained in claim 1 to a dehydrochlorination in the presence of a catalyst comprising at least one member selected from the group consisting of activated carbon and a nickel catalyst.

8. The process for producing 2,3,3,3-tetrafluoropropene according to claim 7, wherein the catalyst comprises the the nickel catalyst.

9. The process for producing 2,3,3,3-tetrafluoropropene according to claim 7, wherein the reaction temperature for the dehydrochlorination reaction is from 200 to 700° C.

10. The process for producing 2-chloro-1,1,1,2-tetrafluoropropane according to claim 1, wherein the catalyst is antimony pentachloride.

11. The process for producing 2-chloro-1,1,1,2-tetrafluoropropane according to claim 1, wherein the solvent comprises carbon tetrachloride and the catalyst is antimony pentachloride.

12. A process for producing 2-chloro-1,1,1,2-tetrafluoropropane, comprising:
reacting 1,2-dichloro-2-fluoropropane with chlorine in the presence of a solvent under irradiation with light to produce 1,1,1,2-tetrachloro-2-fluoropropane, and
reacting the 1,1,1,2-tetrachloro-2-fluoropropane with hydrogen fluoride in the presence of a catalyst to obtain 2-chloro-1,1,1,2-tetrafluoropropane,
wherein the solvent comprises at least one member selected from the group consisting of carbon tetrachloride, 1,1,2-trichloro-1,2,2-trifluoroethane, a C$_{5-8}$ linear perfluoroalkyl compound represented by the formula CF$_3$(CF$_2$)$_n$CF$_3$, wherein n is an integer of from 3 to 6, and a perhalogenated compound, and
wherein the catalyst comprises at least one halide of a metal selected from the group consisting of antimony, niobium, tantalum, tin, titanium, iron and thallium.

13. The process for producing 2-chloro-1,1,1,2-tetrafluoropropane according to claim 12, wherein the light for the irradiation with light in the reacting with chlorine is ultraviolet light containing light with a wavelength of from 200 to 400 nm.

14. The process for producing 2-chloro-1,1,1,2-tetrafluoropropane according to claim 12, wherein the reaction temperature in the reacting with chlorine is from -20 to 60° C.

15. The process for producing 2-chloro-1,1,1,2-tetrafluoropropane according to claim 12, wherein the reaction temperature in the reacting with hydrogen fluoride is from 50 to 200° C.

16. A process for producing 2,3,3,3-tetrafluoropropene, which comprises dehydrochlorinating the 2-chloro-1,1,1,2-tetrafluoropropane obtained in claim 12 in the presence of a catalyst comprising at least one member selected from the group consisting of activated carbon and a nickel catalyst.

17. The process for producing 2,3,3,3-tetrafluoropropene according to claim 16, wherein the reaction temperature in the dehydrochlorinating is from 200 to 700° C.

18. The process for producing 2-chloro-1,1,1,2-tetrafluoropropane according claim 12, wherein the solvent comprises carbon tetrachloride.

19. The process for producing 2-chloro-1,1,1,2-tetrafluoropropane according claim 12, wherein the catalyst is antimony pentachloride.

20. The process for producing 2-chloro-1,1,1,2-tetrafluoropropane according to claim 12, wherein the solvent comprises carbon tetrachloride and the catalyst is antimony pentachloride.

* * * * *